(12) United States Patent
Pauser et al.

(10) Patent No.: US 8,998,610 B2
(45) Date of Patent: Apr. 7, 2015

(54) DISPENSING DEVICE FOR A DENTAL SUBSTANCE

(75) Inventors: Helmut Pauser, Diessen (DE); Manfred Harre, Landsberg am Lech (DE); Andreas Maurer, Langenneufnach (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/321,978

(22) PCT Filed: May 21, 2010

(86) PCT No.: PCT/US2010/035712
§ 371 (c)(1),
(2), (4) Date: Jan. 25, 2012

(87) PCT Pub. No.: WO2010/138401
PCT Pub. Date: Dec. 2, 2010

(65) Prior Publication Data
US 2012/0135375 A1 May 31, 2012

(30) Foreign Application Priority Data

May 29, 2009 (GB) .................................. 0909214.9

(51) Int. Cl.
*A61C 5/04* (2006.01)
*A61C 5/06* (2006.01)
*A61C 9/00* (2006.01)

(52) U.S. Cl.
CPC ............... *A61C 5/062* (2013.01); *A61C 9/0033* (2013.01)

(58) Field of Classification Search
CPC ... A61C 9/0033; A61C 5/062; A61M 25/007; B65B 3/003; B65D 1/00; B65D 35/00; B65D 35/08; B65D 35/30; B29C 45/0001; B29C 45/16

USPC ................ 433/90, 80, 89; 222/386, 391, 388, 222/325–327, 562; 304/264, 272, 523; 264/328.1, 250
See application file for complete search history.

(56) References Cited

U.S. PATENT DOCUMENTS

| | | | | |
|---|---|---|---|---|
| 3,322,307 A * | 5/1967 | Fraser | ........................... | 222/207 |
| 3,638,314 A * | 2/1972 | Lopez et al. | .................... | 433/83 |
| 4,377,380 A * | 3/1983 | Vadas et al. | ..................... | 433/89 |
| 4,998,880 A * | 3/1991 | Nerli | ............................... | 433/80 |
| 5,370,221 A * | 12/1994 | Magnusson et al. | .......... | 206/221 |
| 5,531,255 A * | 7/1996 | Vacca | ........................... | 141/285 |
| 6,508,385 B1 * | 1/2003 | Liardon | ......................... | 222/95 |

(Continued)

FOREIGN PATENT DOCUMENTS

WO  WO 2009/151983   12/2009

OTHER PUBLICATIONS

International Search Report for International Application No. PCT/US2010/035712, filed May 21, 2010.

*Primary Examiner* — Heidi M Eide
(74) *Attorney, Agent, or Firm* — 3M Innovative Properties Company; Qiang Han

(57) ABSTRACT

A dispensing device for a dental substance which comprises a body formed in a single piece. The body connects a first passageway and a second passageway which extend along different paths. The body further comprises a nozzle with a free dispensing end. The second passageway extends into the nozzle and tapers toward the dispensing end. The invention helps to reduce manufacturing costs, and helps facilitating handling of the device.

12 Claims, 3 Drawing Sheets

(56) References Cited

U.S. PATENT DOCUMENTS 6,877,983 B1 * 4/2005 Dragan et al. .................. 433/90
2003/0165793 A1 9/2003 Yobel
2007/0164047 A1 7/2007 Reidt
2007/0172789 A1 7/2007 Muller

* cited by examiner

DISPENSING DEVICE FOR A DENTAL SUBSTANCE

CROSS REFERENCE TO RELATED APPLICATIONS

This application is a national stage filing under 35 U.S.C. 371 of PCT/US2010/035712, filed May 21, 2010, which claims priority to Great Britain Application No.0909214.9, filed May 29, 2009, the disclosures of which are incorporated by reference in their entirety herein.

FIELD OF THE INVENTION

The invention relates to a dispensing device for a dental substance, and in particular to a dispensing device which may be used with an applicator.

BACKGROUND ART

Dental substances are often provided in devices allowing the substance to be dispensed directly to a desired location, for example on a dental pad or in a patient's mouth. Such dispensing devices typically have a chamber for holding the dental substance, an outlet, and a piston for extruding the substance from the chamber through the outlet.

A variety of dispensing devices are designed for dispensation of relatively high viscosity dental substances, like for example dental filling materials. Some of those dispensing devices are configured for use with an applicator providing an extrusion force that is sufficient for dispensation of high viscosity dental substances. In dentistry several types of manually operated applicators are available which provide leverage for increasing manual forces to provide sufficient extrusion forces. Many applicators are designed as a reusable tool which forms part of a dental practice's basic equipment.

Although a variety of applicators and dispensing devices are available there is a desire to provide a dispensing device which can be used with applicators already available in the market. Further it is desirable to provide a dispensing device which is easy to use in combination with such applicators, and which is further relatively inexpensive.

SUMMARY OF THE INVENTION

A first aspect of the present invention relates to a dispensing device for a dental substance. The dispensing device comprises:
  a body formed in a single piece connecting, for fluid communication, a first passageway and a second passageway. The first passageway extends along a first path, and the second passageway extends along a second path, wherein the second passageway forms an undercut with respect to the first passageway.
  The body comprises a nozzle having a dispensing end. The dispensing end may in particular be formed by a free end of the nozzle. The second passageway extends into the nozzle and tapers toward the dispensing end, and
  the second passageway extends entirely through the body.

For the purpose of this specification an "undercut" is preferably a widened cross-sectional area with respect to a passageway that extends along a path from outside into a body, wherein the widened cross-sectional area is greater than substantially any cross-sectional area of the passageway between the widened cross-sectional area and the outside, and wherein any cross-sectional area relates to a cross-section on a plane perpendicularly intersecting the path.

The device of the invention may thus have two differently oriented passageways. The dental substance may be advanced from the first passageway toward the second passageway, from where it can be discharged through the dispensing end to a desired location. The two differently oriented passageways may enable a design of the device which is particularly suitable to guide a substance to a location in a narrow space, for example in a patient's mouth during a dental treatment. For example the device may have a generally elongated portion, and another portion at the dispensing end may be angled or curved away from the elongated portion. Nevertheless the device of the invention preferably allows manufacturing in one piece and a taper of the second path toward the dispensing end. The taper toward the dispensing end preferably provides for a reduction of the flow resistance of the substance in the second passageway relative to a flow resistance of the same substance in a passageway having a uniform cross-section over its length and the same opening dimensions.

The invention is advantageous in that it provides a dental dispensing device which is relatively convenient to use. The device of the invention may require lower forces to dispense the dental substance from the device. For example the taper of the second passageway toward the dispensing end may contribute to such lower forces. Further, the invention enables the dispensing device of the invention to be manufactured by injection molding. The invention may also be advantageous because it allows relatively inexpensive manufacturing of the dispensing device. The dispensing device may be particularly advantageous in use for a dental retraction procedure, for example, for dispensing a relatively high viscosity dental refraction material into a patient's sulcus.

The first and second paths each preferably correspond to a path having a constant curvature, including a curvature of zero. Thus the first and second paths each may correspond to a section of a straight line or a section of a circle, or may substantially correspond to a section of a straight line or a section of a circle.

The first and second paths are preferably different in at least one of curvature, direction in which they extend and/or the plane on which they extend along. Preferably the first and second paths intersect within the body. Further the first and second paths may intersect in an angle of less (or other) than about 180 degrees.

A second aspect of the same invention is an alternative of the first aspect and relates to four alternative embodiments as follows:

In a first alternative embodiment of the second aspect of the invention the dispensing device comprises:
  a body formed in a single piece connecting, for fluid communication, a first passageway and a second passageway;
  the first passageway extending along a first path, and the second passageway extending along a second path, with the first and second paths each extending substantially linear;
  wherein the first and second paths intersect (or approximately intersect) in the body; and
  the body comprising a nozzle having a dispensing end, wherein the second passageway extends into the nozzle and tapers toward the dispensing end.

In a second alternative embodiment of the second aspect of the invention the dispensing device comprises:
  a body formed in a single piece connecting, for fluid communication, a first passageway and a second passageway;
  the first passageway extending along a first path, and the second passageway extending along a second path, with the first path extending substantially linear and the second path extending substantially circular;

wherein the first and second paths meet (or approximately meet) in the body; and the body comprising a nozzle having a dispensing end, wherein the second passageway extends into the nozzle and tapers toward the dispensing end.

In a third alternative embodiment of the second aspect of the invention the dispensing device comprises:

a body formed in a single piece connecting, for fluid communication, a first passageway and a second passageway;

the first passageway extending along a first path, and the second passageway extending along a second path, with the first path extending substantially circular and the second path extending substantially linear;

wherein the first and second paths meet (or approximately meet) in the body; and the body comprising a nozzle having a dispensing end, wherein the second passageway extends into the nozzle and tapers toward the dispensing end.

In a fourth alternative embodiment of the second aspect of the invention the dispensing device comprises:

a body formed in a single piece connecting, for fluid communication, a first passageway and a second passageway;

the first passageway extending along a first path, and the second passageway extending along a second path, with the first and second paths each extending substantially circular;

wherein the first and second paths intersect (or approximately intersect) in the body and/or have a different curvature; and the body comprising a nozzle having a dispensing end, wherein the second passageway extends into the nozzle and tapers toward the dispensing end.

Embodiments in this specification generally relate to all aspects of the invention and may be combined with each embodiment of the different aspects of the invention. Embodiments and/or features of the first and second aspects of the invention may also be combined.

In one embodiment the body forms a container for containing the dental substance. In this embodiment the first passageway may extend into the container. The dental substance may be receivable in the first passageway. The container may further be adapted to receive a piston in the first passageway for advancing the dental substance toward the dispensing end. For example the first passageway may have a generally circular cross-section along the first path. The first passageway may further have a cross-section of generally uniform size along the first path. The piston may have a generally cylindrical shape and may tightly fit into the first passageway. Thus the piston may be adapted to displace the dental substance from the container toward the dispensing end. The piston may have seals, for example annular bulges and/or annular lips, for sealing the piston with walls forming the first passageway.

In a further embodiment the body forms the nozzle, for example in one piece with body. The nozzle may further form or be attached to a cannula. Furthermore the nozzle may be adapted to receive a cannula. The cannula is preferably adapted for direct use in a patient's mouth. For example the cannula may be adapted for insertion into a dental sulcus (a natural space between a tooth and the gums) in a patient's mouth.

The second passageway may extend into the nozzle. Preferably the second passageway is adapted to guide the dental substance received from the first passageway toward the dispensing end. The second passageway may have a generally circular cross-section along the second path. Preferably the second passageway tapers from an inlet diameter of between about 0.5 mm and 6 mm toward a dispensing diameter adjacent the dispensing end of between about 0.05 mm to 5 mm with the dispensing diameter being smaller than the inlet diameter. In a preferred embodiment the second passageway tapers from an inlet diameter of about 1.2 mm to a dispensing diameter adjacent the dispensing end of about 0.4 mm. The second passageway may particularly taper uniformly, although a taper may be likewise realized by steps in the passageway. This may help to reduce the flow resistance of the dental substance in the second passageway which consequently helps reduce the force required to dispense dental substance from the device.

In another embodiment the dispensing device comprises the dental substance and the piston. Dental substances that may be used with the present invention may be selected from among a dental retraction material, a dental impression material, and a dental filling material, for example. A dental refraction material may for example comprise a liquid and a phyllosilicate, in particular a liquid and a combination of at least two different phyllosilicates. The combination of phyllosilicates may for example comprise a layer type 1:1 silicate mineral and a layer type 2:1 silicate mineral. Information about phyllosilicates and their classification can be found in Ullmanns Encyclopedia of Industrial Chemistry (Wiley-VCH), 2005, Silicates; table 4. A dental retraction composition as it may be used with the present invention is disclosed in European patent application EP09161471.9.

In one embodiment the dispensing device of the invention has a cover layer which is connected to the body. Preferably the cover layer forms an outer layer of the container. Further the cover layer may be arranged on the outer container at least partially around the first passageway.

The cover layer in one embodiment is generally opaque, and the body is generally transparent. Thus a device may be provided having a generally transparent body with a transparent nozzle and/or cannula, but with a generally opaque cover. Therefore the device may allow a user to observe the dental material as it flows toward the dispensing end or as it flows within the nozzle and/or cannula. This may for example facilitate precise application of the substance to a desired location, for example in a patient's mouth. On the other hand the cover may protect the dental substance from light prior to the substance flows to the nozzle or cannula. Therefore the dental substance may be storable in the device over a relatively long time, for example several months.

In one embodiment the first passageway over the most part of its length is substantially annularly surrounded by an opaque and generally light blocking cover layer, and the second passageway is at least in an area adjacent the dispensing end generally left open from the cover layer.

The cover layer may further reinforce the container. Thus if for example the dental substance is advanced and thereby a pressure is exerted in the container the cover layer may provide the device with additional strength to prevent cracking or bursting.

In another embodiment the cover layer is more elastic than the body. Therefore if the body cracks or breaks, for example due to improper operation, the cover layer may prevent the device from bursting. Thus the cover layer may help to provide increased reliability of the device.

Preferably the second passageway opens at the dispensing end, which is preferably arranged at a front end of the device. The first passageway may open at a rear end of the device. The piston may close this rear opening. Further the first passageway preferably merges into the second passageway, and particularly may end by merging into the second passageway. The second passageway preferably has a further opening opposite the dispensing end. Thus the body may have at least three openings. Each of the three openings may be closed, for example permanently or non-permanently. Preferably at least one opening of the device is permanently closed.

In one embodiment the end of the second passageway opposite the dispensing end is closed by the cover layer, for example the cover layer may form a bond with the body around the opening and thus permanently close the opening. Therefore the second passageway and the first passageway may form an overall passageway with only two openings—the rear opening of the first passageway and the dispensing end of the second passageway. In other words the embodiment of the device having a cover layer may have only two openings, with the body having three openings of which one opening is closed by the cover layer.

In one embodiment the first and second paths intersect. For example the first path, which the first passageway extends along, may be substantially linear or straight. Further the second path, which the second passageway extends along, may be substantially linear or straight. The first and second paths are preferably arranged at an angle relative to one another. The angle may be between about 30 degrees and 60 degrees, preferably about 43 degrees. This may provide a relatively convenient handling of the device in a patient's mouth. A similar effect may be provided by a further embodiment in which the second path is generally circular, for example corresponds to a section of a circle. Other embodiments in which the first path extends in a general direction, and a second path deflects from that direction are possible.

In a further embodiment the dispensing device of the invention has a catch. The catch preferably extends laterally to the first path. The catch is preferably adapted to retain the device against movement in a direction parallel to the first path. Therefore the catch may allow the dispensing device to be attached to an applicator which can be used to advance the dental substance toward the dispensing end.

The catch may be formed in one piece with the container. Further the catch may be formed partially or entirely with the cover layer. If the cover layer is for example made from a more elastic material than the body the catch may therefore be provided with certain resilience. A resilient catch may allow the use of the device in different applicators because the catch may adopt the size of differently sized receptacles for receiving the device.

The device may further have a resilient adapter, for example in addition to the catch. In this case the catch may be relatively rigid and the resilient adapter may be less rigid than the catch. In particular the adapter may be resilient in a direction laterally to the first path. Therefore the catch may allow the device to be retained by the applicator against relatively high forces (for example resulting from dispensing the dental substance). On the other hand the resilient adapter may still allow the use of the device in different applicators. In this embodiment the catch may be formed in one piece with the body and the resilient adapter may be formed with the cover layer. Further the cover layer itself may form a first resilient adapter and a second resilient adapter may be formed in one piece with the body. A resilient adapter formed in one piece with the body may be provided with certain resilience by an appropriately reduced wall thickness. For example the resilient adapter may be formed by a relatively thin walled structure and the catch may be a more thick walled structure.

In a further embodiment the cover layer forms the resilient adapter. For example the cover layer may be of an elastic material and therefore may be compressible. Further the cover layer may have at least one protrusion that protrudes preferably substantially perpendicular to the first path. Such a protrusion may extend generally along the first path (and protrude perpendicular from the cover layer). Further such a protrusion may extend generally around the first path, for example annularly around the body, (and protrude perpendicular from the cover layer). The protrusion is preferably formed in one piece with the cover layer. The protrusion may have any suitable form, for example may be formed as a bulge or ridges. Multiple protrusions are possible. For example a preferred embodiment has between 3 and 8, most preferably 6 bulges annularly equally distributed around the first path. The protrusions may help to laterally position and/or clamp the device in an applicator.

In another embodiment the dispensing device of the invention is in combination with an applicator for advancing the dental substance from the device. An applicator as it may be used with the present invention is for example available from 3M ESPE AG, Germany under the designation Capsule Dispenser.

Another aspect of the invention relates to a method of manufacturing a dispensing device for a dental substance.

The method comprises the steps of:
providing mold components in positions and shape adapted to form a dispensing device according to the invention, for example one which comprises:
  a body formed in a single piece connecting a first passageway and a second passageway, the first passageway extending along a first path, and the second passageway extending along a second path, wherein the second passageway forms an undercut with respect to the first passageway;
  the body comprising a nozzle having a free dispensing end, wherein the second passageway extends into the nozzle and tapers toward the dispensing end;
  optionally further features as defined in this specification;
providing a moldable material adapted to flow into the mold components; and
molding the moldable material using the mold components to form the dispensing device.

In an embodiment the method comprises the steps of:
providing a mold having a cavity, a first core, and a tapered second core;
wherein the first core and the molded device are separable from one another by relative movement along a first path, and wherein the second core and the molded device are separable from one another by relative movement along a second path which is different from the first path;
positioning the cores such that a front of the first core contacts the second core; and
molding a body in a single piece at least around the area the cores contact each other with the second core extending entirely through the cavity.

The front of the first core may particularly contact a side wall of the second core, for example a side wall in a recess in the second core. This may facilitate retaining the end of the first core in place during molding.

The method thus can provide a device according to the invention. In particular the second passageway may taper toward the dispensing end, and allow the second core to be retracted through the opening opposite the dispensing end. Nevertheless the second passageway may extend along the second path that is different from the first path.

In one embodiment the method further comprises the steps of:
  retracting the second core from the mold;
  repositioning the first core so that a least a portion of the first core extends into the second passageway; and
  molding a cover layer onto the body wherein the second core shapes a wall of the cover layer.

The first core may further be retracted from the first passageway and a third core may be placed into the first passageway. For example instead of the step of repositioning the first core the first core may be replaced by a third core. This third core may be shaped differently than the first core to substantially fill the first passageway and extend into the second passageway.

For molding the cover layer the first or the third core may block the opening of the second passageway opposite of the dispensing end. Thereby molding material may be prevented from penetrating into the first and/or the second channels during the molding step. Further the first and the second channels may thus form an overall passageway with only two openings. Dental substance advanced from the first toward the second passageway may therefore be prevented from leaking from the device.

The body may be made from a plastic material selected from among High density Polyethylene, Polybutylene Terephthalate, Acrylonitrile-Butadiene-Styrene Terpolymer, Polycarbonate, and Polyoxymethylene.

The cover layer may be made from plastic materials selected from among Low density Polyethylene, rubber, Thermoplastic Elastomers, for example Styrene-Butadiene-Styrene Block Copolymer, or Thermoplastic Polyurethane.

DETAILED DESCRIPTION OF THE INVENTION

Figure 1:
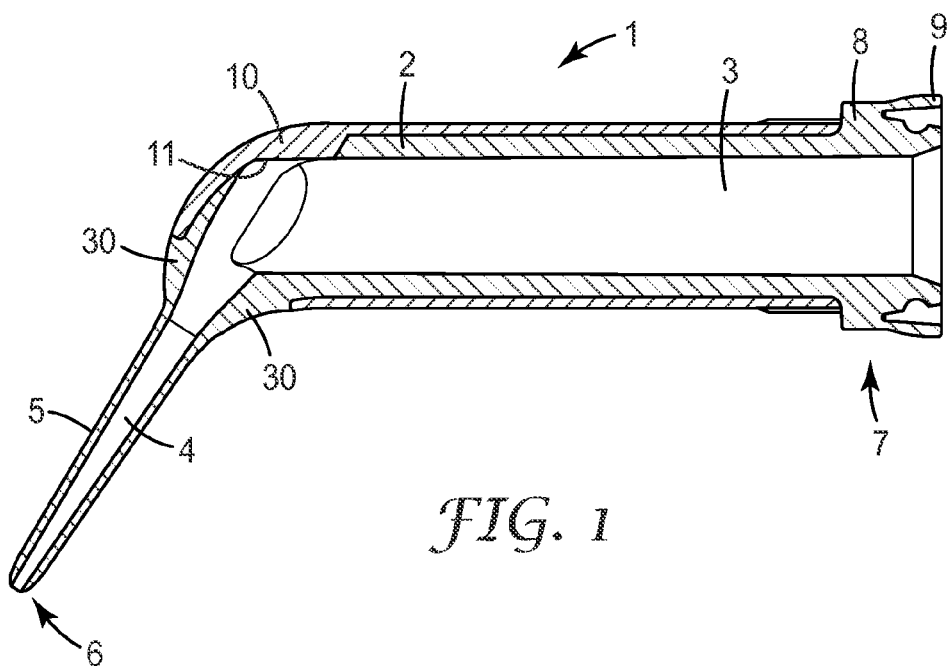
FIG. 1 is a cross-sectional view of a device according to an embodiment of the invention.

FIG. 1 shows a device 1 for containing a dental substance. The device 1 has a body 2, a dispensing end 6 and an adapter end 7. The device 1 may for example be used to dispense the dental substance to a desired location in a patient's mouth. For this purpose the device may, for example, be attached to an applicator (shown in FIG. 2). The body 2 of the device 1 connects a first passageway 3 and a second passageway 4 for fluid communication. The dental substance may be stored in the first passageway 3, and in use of the device advanced toward the second passageway 4. The device 1 has further a nozzle 5 through which the dental substance may be extruded when the device is used. In the example shown, the nozzle 5 forms a cannula. The cannula is preferably adapted to dispense the dental substance directly into a patient's mouth. In another example the nozzle may also be adapted to receive a separate cannula having a desired shape, for example one that is adapted to dispense the dental substance directly into a patient's mouth.

A cover layer 10 extends over a part of the outer surface of the body 2. The cover layer 10 preferably tightly adheres on the body 2, which can for example achieved by molding the cover layer onto the pre-molded body or vice versa. Thereby the person skilled in the art will understand that the molding materials and molding parameters may be appropriately selected to achieve a good bond between the body and the cover layer. The cover layer covers, preferably seals, an auxiliary opening 11 in the body 2. The auxiliary opening 11 is formed in the body 2 by the second passageway 4 opposite the dispensing end 6. Thus the body comprises three openings, but the auxiliary opening 11 is closed by the cover layer 10. Accordingly the first and second passageways 3, 4 connect the remaining two openings. Therefore the first and second passageways 3, 4 form a fluid tight overall passageway through the device 1. The auxiliary opening may be useful in manufacturing of the device according to the invention as described below, but is preferably covered or closed for use of the device. The body 2 may be molded by providing a molten plastic material into a mold. The molten plastic material may be injected through a gate of the mold. The gate of the mold may be positioned adjacent the adapter end 7. Therefore the hot plastic material may be caused by injection to flow in the mold in an overall flow direction from the adapter end 7 toward the dispensing end 6. Thereby the hot plastic material may initially flow generally laterally to the overall flow direction and annularly around a mold core. The material flow is typically split by the mold core at one side and remerges at the opposite side so that a ring of material around the core is formed. Further as additional material is injected the material will typically flow toward the dispensing end 6 in the form of a ring shaped material flow. The ring shaped material typically forms a joint line in an area where the material remerged behind the core, and that joint line typically continues over the length the material flows forward. The joint line may form an area in which the tensile strength of the solidified plastic is reduced relative other portions.

The body 2 preferably has an annular thickened portion 30 in a transition area between the nozzle 5 and the remaining body portion toward the adapter end 7. It has been found that the joint line that may exist in the remaining body portion typically does not continue into the nozzle when such a thickened portion 30 is present. In contrast if the thickened portion 30 is not present the joint line typically continues into the nozzle. The thickened portion 30 thus may help to maximize the pressure stability of the nozzle, and/or to mini the wall thickness of the nozzle.

The passageway 3 is adapted to receive a piston (not shown). The piston is preferably adapted to seal with the walls forming the first passageway 3 and is preferably movable in the first passageway for advancing the dental substance toward the dispensing end. The piston may be formed by a generally cylindrical member having annular ridges which form seals, for example. The piston may further have a front that is shaped such that a dead space is reduced or eliminated when the piston is moved in the front most position. This may for example be achieved by complementary shaped cooperating surfaces at the piston and the end of the passageway. Further the piston may provide a, preferably hermetic, seal for one opening of the first passageway 3. The device may further be provided with a cap (not shown) for preferably hermetically sealing an opening of the second passageway 4 adjacent the dispensing end 6.

Therefore the device may be adapted to hermetically seal the dental substance in the overall passageway formed by the first and second passageways 3, 4. Therefore the device may help achieving a relatively long shelf life for the dental substance stored therein, for example a shelf life of several months. Thereby the dental substance may be sufficiently protected from the environment so that it still can be used after a storage time as mentioned.

The second passageway 4 extends into the nozzle 5 and tapers toward the dispensing end 6. For example the nozzle 5 may have a conical passageway. The second passageway adjacent the dispensing end has preferably a relatively narrow cross-section. The cross-section adjacent the dispensing end may be about 0.4 mm in diameter. The cross-section adjacent the transition of the second passageway 4 and the first passageway 3 may be about 1.2 mm. Such dimensions may be particularly advantageous in combination with a dental retraction composition as it is disclosed in European patent application no. EP09161471.9. Other dimensions are possible though, dependent on the substance used with the device. A relatively small dimension of the opening adjacent the dispensing end may allow the dental substance to be dispensed as a relatively fine strand from the nozzle. Although the second passageway adjacent the dispensing end may be relatively narrow the flow resistance for the dental substance when forced toward the dispensing end 6 may still be acceptable because of the taper toward the dispensing end. In particular the flow resistance in the tapered passageway may be lower than, for example, the flow resistance resulting from forcing the same substance through a passageway having a uniform cross-section over its length. With the tapered geometry of the second passageway the force required to extrude a dental retraction composition was reduced by about 40% relative to a force required to extrude the same substance through a passageway having a uniform cross-section over its length.

EXAMPLE

The extrusion force for extruding a dental retraction composition through a tapered nozzle was compared to the extrusion force for extruding the same material through a non-tapered nozzle (one having a generally uniform dimension over its length).

The tapered nozzle had a passageway with an outlet opening having a diameter of about 0.4 mm. The nozzle and the passageway had a length of about 7.6 mm. An inlet opening of the passageway was provided opposite of the outlet. The taper was about 3 degrees measured in a plane along about the center of the passageway between opposing side walls of the passageway.

The non-tapered nozzle had a passageway with an outlet opening having a diameter of about 0.4 mm. The nozzle and the passageway had a length of about 7.6 mm. An inlet opening of the passageway was provided opposite of the outlet. The passageway had a diameter of about 0.4 mm over the entire length of the cannula.

The composition used for the test corresponded to a composition having the following formulation:
  liquid in an amount from about 15 wt.-% to about 50 wt.-% or from about 16 wt.-% to about 40 wt.-% or from about 17 wt.-% to about 30 wt.-%.
  layer type 1:1 silicate mineral in an amount from about 1 wt.-% to about 34 wt.-% or from about 2 wt.-% to about 30 wt. % or from about 2.5 wt.-% to about 25 wt.-%.
  the layer type 2:1 silicate mineral in an amount from about 30 wt.-% to about 65 wt.-% or from about 31 wt.-% to about 64 wt.-% or from about 32 wt.-% to about 63 wt.-%.
  astringent in an amount from about 0.01 wt.-% to about 30 wt.-% or from about 5 wt.-% to about 20 wt.-% or from about 10 wt.-% to about 15 wt.-%.
  additives in an amount from about 0.0001 wt.-% to about 10 wt.-% or from about 1 wt.-% to about 7 wt.-% or from about 2 wt.-% to about 5 wt.-%.

The extrusion force was measured as follows:

The extrusion force was measured using as testing device a Zwick Z020 machine (Zwick Roell Comp.). The testing device was equipped with a holder for containers and a small stamp to press against the piston inserted in the container and sealing the reservoir. The dimensions of the stamp corresponded to those used in commercially available single container dispensers (commercially available e.g. from 3M ESPE Comp.; order code 5706 SD). The feeding speed was set to 1.0 mm/s. The force was measured after the initial yield point was overcome (about 6-9 mm from starting point). The extrusion force was determined as an average value out of six individual measurements.

Result:

The extrusion force measured on the tapered nozzle was about 135 N, and the extrusion force measured on the non-tapered nozzle was about 190 N.

The device 1 shown in FIG. 1 has a catch 8 which is adapted to be received in a dental applicator. The catch is formed as an annular rim around a portion of the body. The catch 8 allows the device to be retained in the applicator such that the device is prevented from moving when the applicator is used to advance the dental substance.

Furthermore the device 1 has a resilient adapter 9. The resilient adapter 9 is formed as an annular ring which is connected to the catch. The ring has a wall thickness which is reduced relative to the wall thickness of the catch. Therefore the resilient adapter is less rigid than the catch although the catch and the resilient adapter may be made from similar materials. The resilient adapter may have a greater dimension than the catch. Measures of the catch and the resilient adapter are specified in UK patent application 0909167.9 and may also be used in combination with the present invention. Preferably the resilient adapter allows the device to be clamped in an applicator. The clamping may be advantageous in that it slightly restrains the device against rotation in the device. A user may therefore be able to adjust the orientation of the cannula of the device relatively precisely and permanently.

Figure 2:
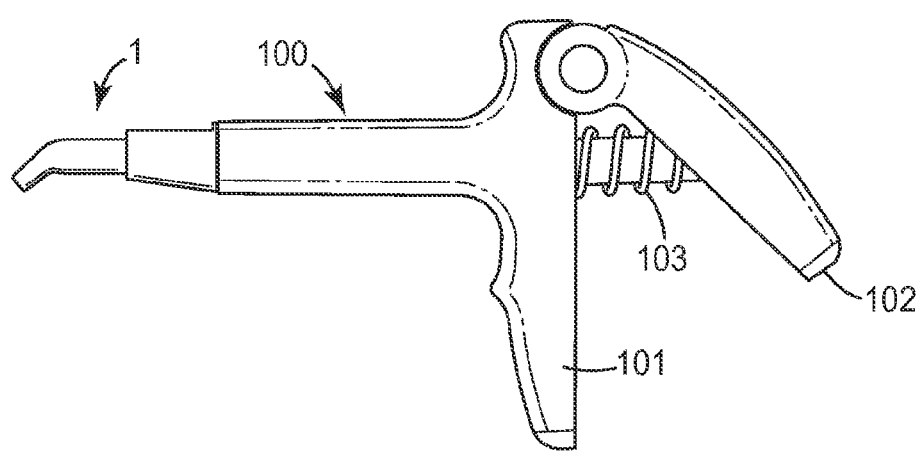
FIG. 2 is a view of the device of FIG. 1 in combination with an applicator according to an embodiment of the invention.

FIG. 2 shows the device 1 in cooperation with an applicator 100. The applicator shown is for example available from 3M ESPE AG, Germany under the designation Capsule Dispenser. The applicator has a pair of handles 101, 102 and a plunger 103 that can be advanced against spring load by the handle 102. The plunger can extend into the device 1 to advance the piston (not shown) of the device for urging the dental substance toward the dispensing end of the device 1 while the device is retained in the applicator.

Although the device of the invention can be made in any suitable manner, it is preferably made by injection molding. Therefore FIGS. 3 and 4 show one example of a mold and illustrate some steps for molding the device using the exemplary mold.

Figure 3:
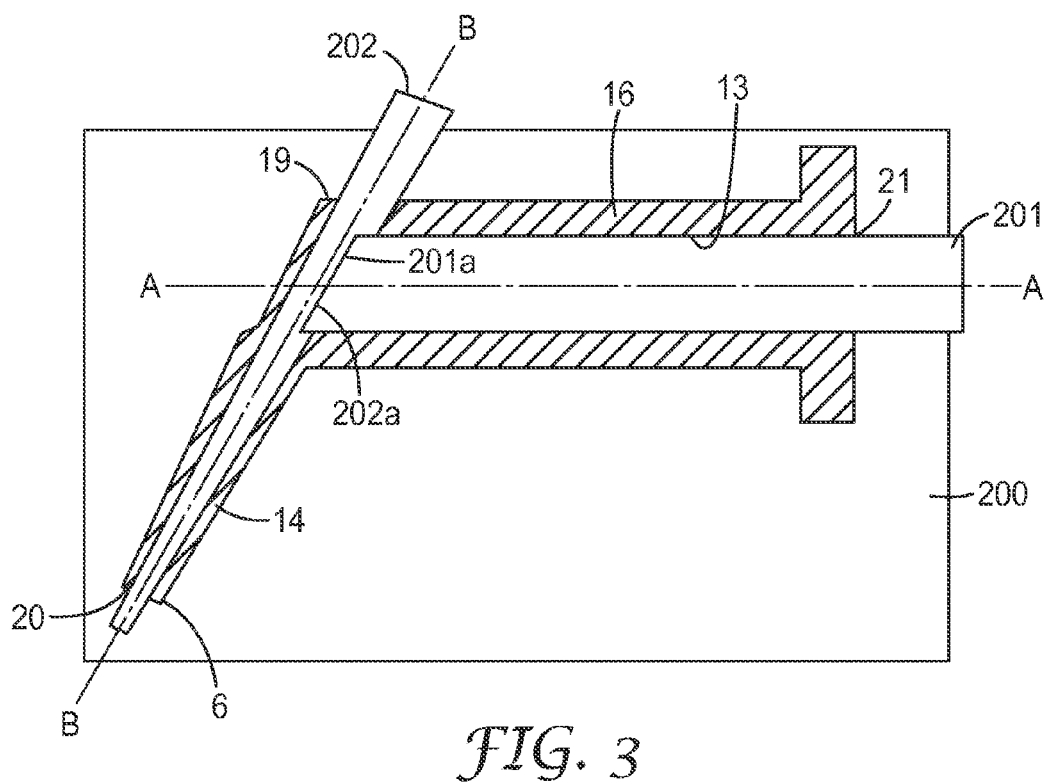
FIG. 3 is a cross-sectional view of a device in mold in a manufacturing step according to an embodiment of the invention.

FIG. 3 shows a molded body 16 in a cavity of a mold 200. A first core 201 and a second core 202 are provided in the mold 200. The first core is movable along the path A, and the second core is movable along the path B. The person skilled in the art will appreciate that instead of or in addition to moving the first and/or second core(s) the molded device may be moved, for example when the molded device is removed from the mold and the cores. Therefore the mold and/or the core(s) may generally be adapted to provide for relative movement between the cores and the molded device. In the embodiment shown in the example, the paths A, B are angled with respect to one another. The first and second cores 201, 202 are shown in a molding position in FIG. 3, which allows molding of the body according to the invention. Thereby the first core 201 shapes a first passageway 13, and the second core 202 shapes a second passageway 14. In the molding position a front 201a of the first core 201 contacts the second core 202, in the example a side 202a of the second core 202. The second core 202 and the first core 201 may therefore have cooperating surfaces that abut in the molding position of the cores.

Liquid material injected in the mold during molding may therefore be prevented from penetrating between the abutting surfaces 201a, 202a of the cores 201, 202 respectively. Further the second core 202 extends entirely through the body 16, and the first core extends only partially into the body. Thus the second passageway 14 along the path B extends entirely through the body 16. The first passageway 13 along path A in contrast does not extend entirely through the body 16, but merges into the second passageway 14. This means that at the manufacturing stage illustrated in FIG. 3 the body has three openings. The first passageway 13 forms a first opening in the body 16. The first opening may correspond to a rear opening 21 of the device which preferably is adapted to receive a piston for advancing dental substance from the device. A second opening is formed by the second passageway 14 and preferably forms a dispensing opening 20 which enables for dental substance to be dispensed from the device. The second passageway 14 further also forms an auxiliary opening 19 in the body 16 opposite the dispensing opening through which the second core 202 can be retracted. The core 202 is preferably tapered and thus adapted to shape a tapered passageway in the body 16. The configuration illustrated in FIG. 3 enables molding of a nozzle having a second passageway that tapers toward the dispensing end, and is angled relative to the first passageway.

Figure 4:
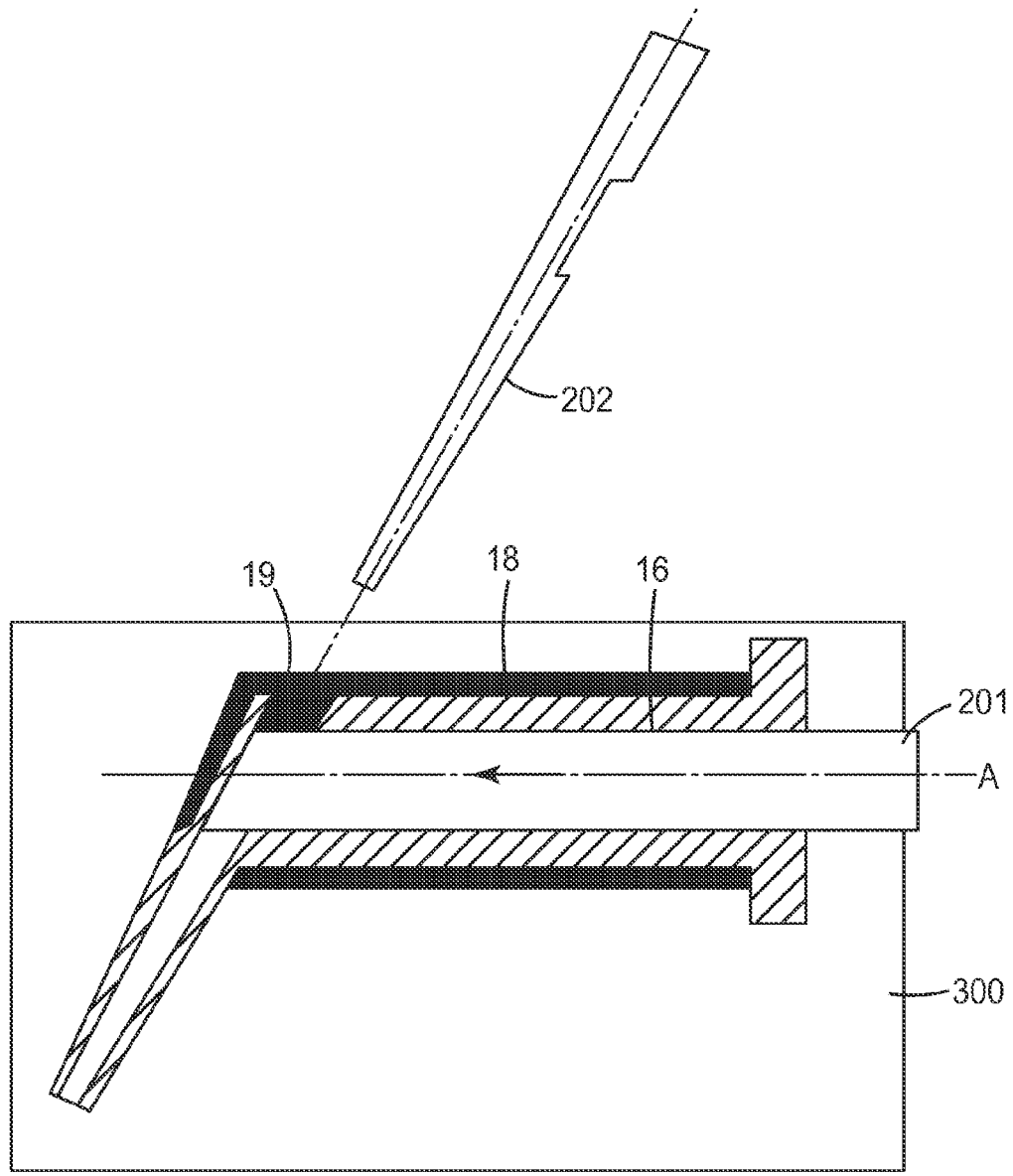
FIG. 4 is a cross-sectional view of the device in mold in another manufacturing step according to an embodiment of the invention.

FIG. 4 relative to FIG. 3 shows the molded body 16 in a subsequent manufacturing step. The body 16 in the example is placed in a mold 300 having a cavity which has a portion that is oversized with respect to the body 16. Thus a space is formed between the cavity wall and part of the outer surface of the body 16. The core 202 is refracted from the body 16, and the core 201 is positioned toward the space cleared by the retracted core 202. Thereby the core 201 preferably covers the auxiliary opening 19. This position of the cores allows for over-molding of the body 16. The figure shows the body 16 already over-molded by the cover layer 18. The cover layer 18 extends over a part of the outer surface of the body 16 and also covers the auxiliary opening 19. During the molding step the core 201 seals the auxiliary opening. Therefore liquid molding material is preferably prevented from penetrating into the first and/or the second channels. After removal of the device from the mold and the cores the embodiment illustrated in FIG. 4 may generally correspond to the device illustrated in FIG. 1.

Accordingly features described for one embodiment may likewise be used in other embodiment as described in this specification.

The invention claimed is:

1. A dispensing device for a dental substance, comprising: a body formed in a single piece connecting a first passageway and a second passageway, the first passageway extending along a first path and having an opening at a rear end of the device, and the second passageway extending along a second path, wherein the second passageway forms a widened cross-sectional area, the body comprising a nozzle having a dispensing end, wherein the second passageway extends into the nozzle, tapers toward the dispensing end and opens at the dispensing end and wherein the second passageway has a second opening opposite the dispensing end; and a cover layer which is connected to the body, wherein the second opening of the second passageway opposite the dispensing end is closed by the cover layer so that the second passageway and the first passageway form an overall passageway with only two openings, the opening of the first passageway and the dispensing end.

2. The dispensing device of claim 1, wherein the body forms a container for containing the dental substance in the first passageway, wherein the container is adapted to receive a piston in the first passageway for advancing the dental substance toward the dispensing end.

3. The dispensing device of claim 2, comprising the dental substance and the piston.

4. The dispensing device of claim 1, wherein the cover layer forms an outer layer of the container around the first passageway.

5. The dispensing device of claim 1, wherein the cover layer is more elastic than the body.

6. The dispensing device of claim 1, wherein the first passageway ends by merging into the second passageway, and wherein the first and second paths are substantially linear and arranged in an angle relative to one another.

7. The dispensing device of claim 6, wherein the angle is about 43 degrees.

8. The dispensing device of claim 1, further having a catch which extends laterally to the first path, and being adapted to retain the device against movement in a direction parallel to the first path.

9. The dispensing device of claim 1, in combination with an applicator for advancing the dental substance from the device.

10. A Method of manufacturing a dispensing device for a dental substance, comprising the steps of:
providing a mold in positions and shape adapted to form a dispensing device according to claim 1; providing a moldable material adapted to flow into the mold; and molding the moldable material using the mold to form the dispensing device.

11. The method of claim 10, further comprising the steps of:
the mold having a cavity, a first core, and a tapered second core; wherein the first core and the molded device are separable from one another by relative movement along a first path, and wherein the second core and the molded device are separable from one another by relative movement along a second path which is different from the first path;
positioning the cores such that a front of the first core contacts the second core; and
molding the body in a single piece at least around the area the cores contact each other with the second core extending entirely through the cavity.

12. The method of claim 10, further comprising the steps of:
retracting the second core from the mold;
repositioning the first core so that a least a portion of the first core extends into the
second passageway; and
molding the cover layer onto the body wherein the second core shapes a wall of the cover layer.

* * * * *

UNITED STATES PATENT AND TRADEMARK OFFICE
CERTIFICATE OF CORRECTION

PATENT NO. : 8,998,610 B2
APPLICATION NO. : 13/321978
DATED : April 7, 2015
INVENTOR(S) : Helmut Pauser et al.

Page 1 of 1

It is certified that error appears in the above-identified patent and that said Letters Patent is hereby corrected as shown below:

IN THE SPECIFICATION

Column 2

Line 31, delete "refraction" and insert -- retraction --, therefor.

Column 4

Lines 20-21, delete "refraction" and insert -- retraction --, therefor.

Column 7

Line 4 (Approx.), delete "a least" and insert -- at least --, therefor.

Column 9

Line 60, delete "30 wt. %" and insert -- 30 wt.-% --, therefor.

Column 11

Line 40, delete "refracted" and insert -- retracted --, therefor.

IN THE CLAIMS

Column 12

Line 35 (Approx.), In Claim 10, delete "Method" and insert -- method --, therefor.

Column 12

Line 60 (Approx.), In Claim 12, delete "a least" and insert -- at least --, therefor.

Signed and Sealed this
Twenty-third Day of February, 2016

Michelle K. Lee
*Director of the United States Patent and Trademark Office*